(12) United States Patent
Dudley

(10) Patent No.: US 8,334,414 B2
(45) Date of Patent: Dec. 18, 2012

(54) COMPOUNDS AND METHODS OF ARYLMETHYLATION (BENZYLATION) AS PROTECTION FOR ALCOHOL GROUPS DURING CHEMICAL SYNTHESIS

(75) Inventor: Gregory Dudley, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 37 days.

(21) Appl. No.: 12/821,525

(22) Filed: Jun. 23, 2010

(65) Prior Publication Data

US 2010/0256383 A1 Oct. 7, 2010

Related U.S. Application Data

(62) Division of application No. 11/399,300, filed on Apr. 6, 2006, now Pat. No. 7,754,909.

(60) Provisional application No. 60/668,699, filed on Apr. 6, 2005, provisional application No. 60/708,580, filed on Aug. 16, 2005.

(51) Int. Cl.
*C07C 41/00* (2006.01)

(52) U.S. Cl. ........................................................ 568/686

(58) Field of Classification Search .................... None
See application file for complete search history.

(56) References Cited

PUBLICATIONS

Poon et al., Synlett (2005), (20), 3142-3144.*

* cited by examiner

*Primary Examiner* — Karl J Puttlitz
(74) *Attorney, Agent, or Firm* — Allen, Dyer, Doppelt, Milbrath & Gilchrist P.A.

(57) ABSTRACT

A process for benzylating an alcohol includes mixing 2-benzyloxy-1-methylpyridinium triflate in an aromatic hydrocarbon solvent having a predetermined boiling point; adding an acid scavenger to the mixture; combining the alcohol to be benzylated with the mixture; reacting the alcohol with the 2-benzyloxy-1-methylpyridinium triflate by heating above ambient temperature to generate the benzylated alcohol; and separating the benzylated alcohol from the mixture.

6 Claims, 13 Drawing Sheets

*objective:*

6          7

COMPOUNDS AND METHODS OF ARYLMETHYLATION (BENZYLATION) AS PROTECTION FOR ALCOHOL GROUPS DURING CHEMICAL SYNTHESIS

RELATED APPLICATION

This application is a division of U.S. application Ser. No. 11/399,300 which was filed on Apr. 6, 2006 now U.S. Pat. No. 7,754,909, and which claimed priority from U.S. provisional application Ser. No. 60/668,699, filed on Apr. 6, 2005, and U.S. provisional application Ser. No. 60/708,580 filed on Aug. 16, 2005.

FIELD OF THE INVENTION

The present invention relates to the field of chemical organic synthesis and, more particularly, to compounds and methods for benzylation and arylmethylation of alcohol groups as protection of the alcohol group during chemical synthesis.

BACKGROUND OF THE INVENTION

The complexities of natural product synthesis and of the rapidly developing field of carbohydrate synthesis create a demand for chemically differentiable protecting groups (PGs) for vulnerable functionality. Benzyl ethers are among the most popular alcohol Pgs due to their ease of formation, stability to a wide range reaction conditions, and mild cleavage protocols. Modified arylmethyl PGs have been tailored for use in more complex systems.

Several arylmethyl PGs are cleaved by initial transformation into a para-hydroxbenzyl (PHB) ether. Jobron and Hindsgaul first reported the use of O-protected 4-O-benzyl PGs for carbohydrate chemistry. Removal of the arene 4-O-PG under the appropriate conditions reveals the PHB ether, which is then easily hydrolyzed. Cross-coupling of para-bromobenzyl (PBB) ethers provides a similar effect: palladium-catalyzed amination of the PBB group yields a labile para-aminobenzyl ether, whereas palladium-catalyzed borylation of PBB followed by oxidation afforded a PHB ether in a synthetic approach to ciguatoxin.

These past efforts reflect the importance of diverse arylmethyl PGs and highlight the need for orthogonality and functional group compatibility in the cleavage event.

As noted above, benzyl ethers are among the most common and important protecting groups in organic synthesis. Like other alkyl ethers, they are advantageous for their stability to a wide range of reaction conditions and for the minimal electronic impact that they impart on the oxygen atom to which they are attached. For example, benzyl ethers are often employed to establish chelation control during addition to chiral aldehydes, which provides selectivity opposite that predicted by the acyclic Felkin-Anh model and observed with bulky silyl ethers. Similarly, benzyl-protected glycosyl donors are "armed" relative to acylated analogues. Among alkyl ethers, benzyl (and modified arylmethyl)ethers are perhaps the most versatile with respect to modes of cleavage, which include hydrogenolysis, oxidation, and acidic decomposition under a range of experimental protocols.

Relatively harsh conditions are typically required for generating benzyl ethers from the corresponding alcohol, with the two most popular protocols being (1) the Williamson ether synthesis, an SN2-type reaction between alkali metal alkoxides and benzyl bromide, and (2) coupling using benzyl trichloroacetimidate, which is generally promoted by trifluoromethanesulfonic acid (triflic acid, TfOH). Typical benzylation reactions are thus limited to substrates that tolerate either strongly acidic or basic conditions. β-Hydroxy esters, for example, are subject to several acid- or base-catalyzed reactions, including retro-Aldol, elimination, and epimerization of stereogenic centers—to the carbonyl group. Benzylation of these ubiquitous intermediates in the synthesis of polyketides and other important compounds can be problematic. Selective protection of polyol systems (e.g., carbohydrates) can also be complicated by base-catalyzed migration of esters and silyl ethers and by acid-catalyzed cleavage of silyl ethers and acetal linkages.

A recent review addresses the myriad options for protecting alcohols using mild, convenient, and environmentally friendly conditions, but no methods for the formation of benzyl ethers are discussed. Silylation and acylation of alcohols can be accomplished under effectively neutral conditions using activated reagents that react with the free alcohol. Imidazole and DMAP are frequently employed to activate silyl and acyl chlorides; conveniently, they are also capable of scavenging any acid that is produced during the course of the reaction. Protonation of benzyl trichloroacetimidate provides an activated reagent that reacts with free alcohols, but this mode of activation precludes neutralization of free acid. In principle, covalent activation (alkylation) of a trichloroacetimidate surrogate would enable the formation of benzyl ethers in the absence of external base or acid and in the presence of acid scavengers (if desired).

Accordingly, benzylation of alcohols under mild and nearly neutral conditions, as disclosed herein, would constitute a significant advance in synthetic chemistry. Thus, it was envisioned that 2-benzyloxypyridine could serve as an imidate surrogate for benzylation of alcohols. Pyridinium salts have been employed in esterification reactions, with Mukaiyama's 2-chloro-1-methylpyridinium iodide being perhaps the most popular.

Conversion of alcohols into thioesters and azides using 2-fluoro-1-methylpyridinium tosylate has also been demonstrated. The two pieces of prior knowledge that were most influential in guiding the current work are: (1) certain 2-alkoxypyridinium bromides decompose to bromoalkanes and pyridones; and (2) 2-alkoxypyridinium sulfonates do not proceed spontaneously to alkyl sulfonates. It was hypothesized that decomposition of 2-alkoxypyridinium sulfonates in the presence of alcohols would give rise to alkyl ethers and pyridones, and preliminary data in support of this hypothesis was reported from this laboratory.

SUMMARY OF THE INVENTION

With the foregoing in mind, the present invention advantageously provides compounds and methods for benzylation of alcohol groups as a means of protection of the alcohol group during chemical synthesis.

This laboratory recently reported that aryl-siletanes (-silacyclobutanes) react with hydrogen peroxide under mild conditions to afford phenols. See the publication by Sunderhaus, J. D.; Lam, H. and Dudley, G. B.; Oxidation of Carbon-Silicon Bonds: The Dramatic Advantage of Strained Siletanes; Org. Lett. 2003, 5, 4571-4573; which is incorporated herein by reference in its entirety. The oxidation reaction (silylarene to phenol) dramatically increases the oxidation potential (electron density) of the arene ring.

Seeking to take advantage of this change, it was an object to develop a new arylmethyl PG for alcohols, the cleavage of which would be triggered by hydrogen peroxide. Unlike masked PHB ethers, latent PHB ethers offer greater promise in terms of orthogonality with a range of other common PGs. for example, revealing the PHB intermediate does not involve cleavage of a different protecting group.

Herein disclosed is the synthesis and application of a siletane-substituted benzyl PG for alcohols and phenols, as shown in FIG. 1. Para-Siletanylbenzyl (PSB) derivatives 1a and 1b were prepared from commercially available compound 7 according to FIG. 2.

Also disclosed are the synthesis and reactivity of 2-benzyloxy-1-methylpyridinium triflate (compound 1), a novel benzylation reagent for alcohols. Salt 1 is easy to prepare, bench-stable, and pre-activated. No acidic or basic promoters are needed for benzyl transfer, which occurs simply upon warming in the presence of the alcohol substrate.

Typical prior art benzylation protocols are shown in FIG. 6, wherein the objective of the present invention is indicated in the lower structural formula shown.

Herein are described the synthesis and reactivity of 2-benzyloxy-1-methyl-pyridinium triflate (Bn-OPT, 1), which provides benzyl ethers simply upon warming in the presence of a free alcohol. The overall balanced equation for the benzylation of alcohols (2→3) is shown in FIG. 7. Oxypyridinium triflate 1 may eventually supplant benzyl trichloroacetimidate for the synthesis of benzyl ethers from alcohols.

BRIEF DESCRIPTION OF THE DRAWINGS

Some of the features, advantages, and benefits of the present invention having been stated, others will become apparent as the description proceeds when taken in conjunction with the accompanying drawings, presented solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Para-Siletanylbenzyl (PSB) Ether as a Benzylating Protective Group.

Herein disclosed is a novel arylmethyl protecting group that is electronically similar to benzyl (Bn) but that can be cleaved under mild oxidizing conditions in the presence of para-methoxybenzyl (PMB). para-Siletanylbenzyl (PSB) ethers are formed in one or two steps from the corresponding alcohols and cleaved in one or two steps with basic peroxide. Alcohols and phenols have been protected in good yields and deprotected cleanly under mild oxidative conditions, for example, with hydrogen peroxide.

Figure 1:
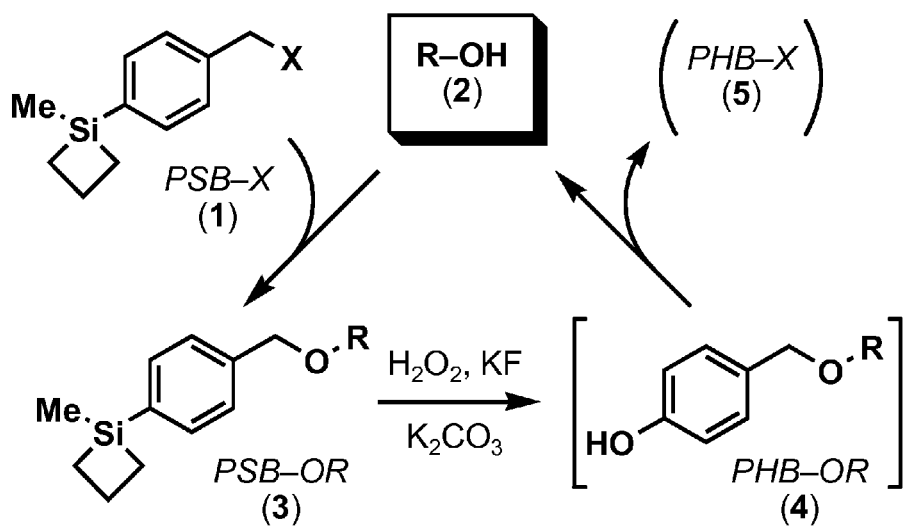
FIG. 1 is an overview of protection/deprotection of alcohols using the para-siletanylbenzyl protecting groups, according to an embodiment of the present invention.
Figure 2:
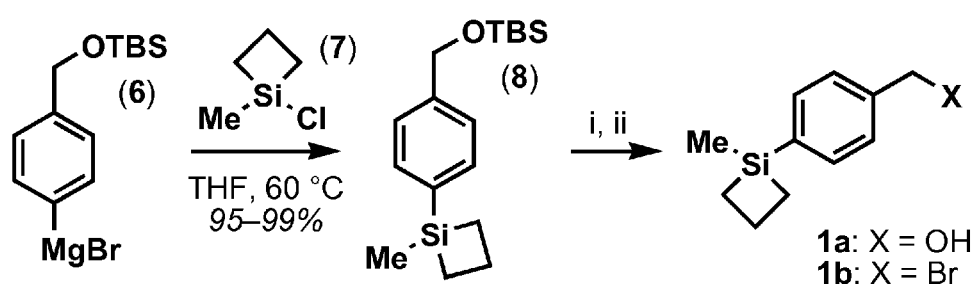
FIG. 2 shows preparation of 1a and 1b: (i) HCl, MeOH, 3 h, 94% (1a); (ii) $CBr_4$, $PPb_3$, 12 h, 95% (1b)

Arylmagnesium bromide, compound 6 in FIG. 2, couples with siletane 7 to provide 8 in excellent yield. The silyl ether is then selectively removed in acidic methanol to afford PSB alcohol 1a. The fact that the arylsiletane is unaffected by these conditions is encouraging with respect to the potential utility of PSB ethers. PSB-OH (1a) then yields PSB-Br (1b) upon treatment with $CBr_4$ and $PPh_3$.

Figure 3:
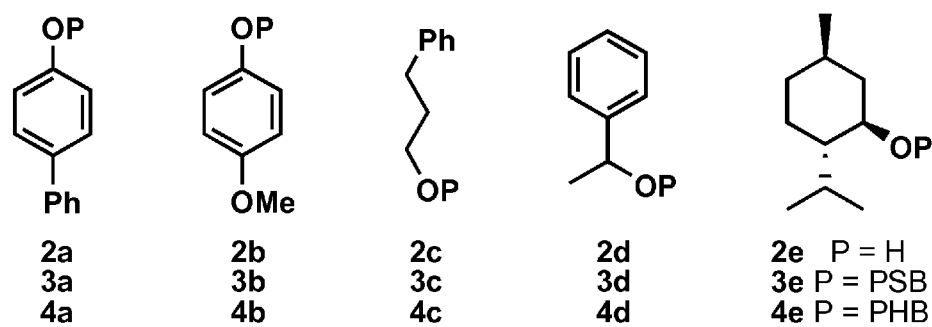
FIG. 3 depicts alcohols and PSB ethers described in Tables 1 and 2.

We selected a representative sample of aromatic and aliphatic alcohols to serve as test cases for the formation and cleavage of PSB ethers and these can be seen in FIG. 3.

Protection of phenols can be achieved using PSB-OH (1a) under Mitsunobu conditions (Table 1, entries 1 and 4). Those of skill in the art will recognize that the term "Mitsunobu conditions" is explained in Hughes, D. L.; *Org. React.* 1992, 42, 335-656; a publication which is incorporated herein by reference in its entirety. Attempts to alkylate potassium, cesium, or sodium salts with 1b were unsuccessful (entries 2 and 6). Arylmethylation of primary alcohols (i.e., 2c) occurs smoothly with PSB-Br (1b) using freshly prepared $Ag_2O$; this afforded the corresponding PSB ether in 80-83% yield (entry 5). However, secondary alcohols could not be protected efficiently using the same method even after prolonged reaction times (entries 7 and 8). Side products and/or low conversions were observed.

Figure 4:
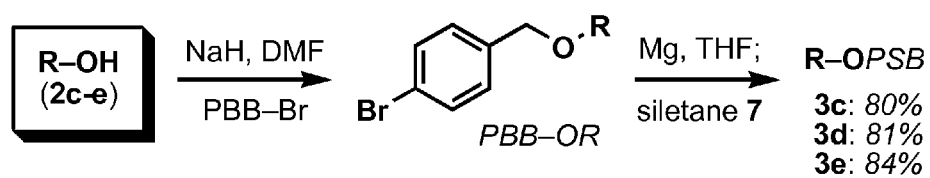
FIG. 4 shows a two-step protection of alcohols and its overall yields.

A two-step protection strategy was adopted for such substrates (FIG. 4). The alcohol is first derivatized as a PBB ether, which is then silylated via the corresponding Grignard reagent. This circumvents the independent synthesis of 1 and increases the scope of PSB protected alcohols. The alternative protocol may be useful for protection of alcohols prior to introducing sensitive functionality.

With PSB ethers in hand, the deprotection was investigated using conditions identified previously in our laboratory. Tamao-type oxidation of aryl ethers in 3a and 3b provides the deprotected phenols (2a and 2b) in one step (Table 2, entries 1 and 2). Intermediate PHB ethers 4a and 4b undergo solvolysis during the course of the reaction.

In the aliphatic ether cases (3c-e), the labile PHB ethers (4c-e) were isolated and then cleaved using $FeCl_3$ (entries 3-5, 7) or DDQ (2,3-dichloro-5,6-dicyano-1,4-benzoquinone; entry 6) to give alcohols 2c-e. Alternatively, Woerpel's more rigorous carbosilane oxidation protocol also affords the PHB ethers (4c and 4d, entries 6 and 7). Such conditions are not expected to tolerate pendant silyl ether PGs, but they do afford excellent yields after a relatively simple purification. PSB ethers can also be removed by hydrogenolysis (entry 8).

Figure 5:
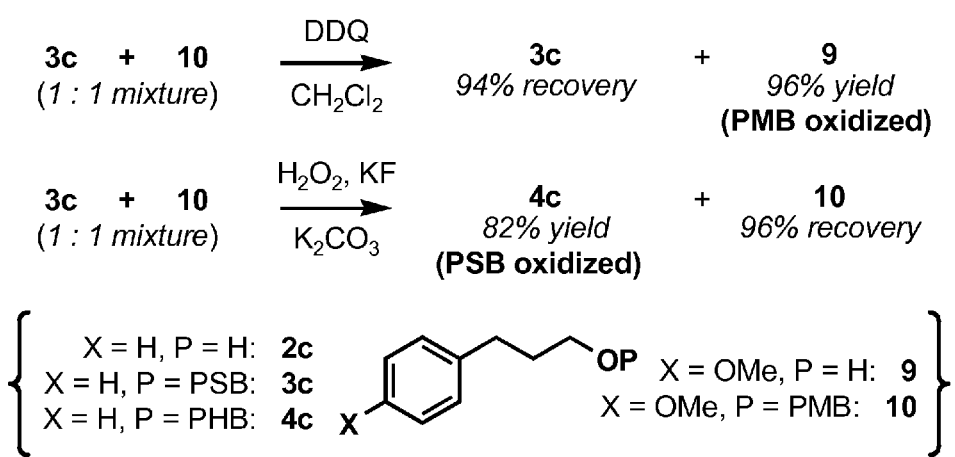
FIG. 5 indicates orthogonality in the oxidative cleavage of para-siletanylbenzyl (PSB) and para-methoxybenzyl (PMB) ethers.
Figure 6:
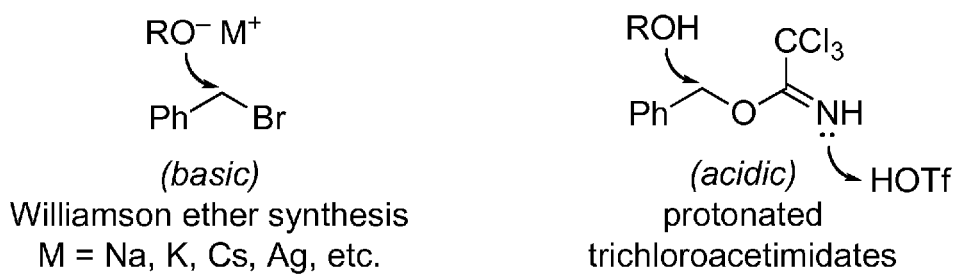
FIG. 6 shows standard prior art benzylation protocols (above) and one approach of the present invention (below)
Figure 6:
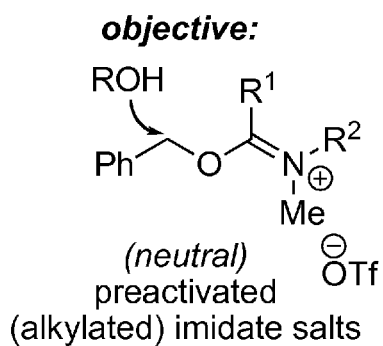
Figure 7:
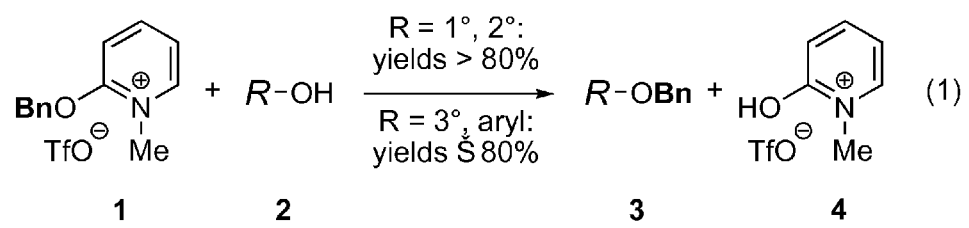
FIG. 7 illustrates the balanced equation for benzylation of alcohols.

PSB ethers are presumably similar to benzyl ethers in terms of arene oxidation potential, yet they cleave under mild oxidizing conditions that are unique among the common arylmethyl PGs. This attractive feature is shown herein through competition experiments with para-methoxbenzyl (PMB) ether 10. PMB ethers can be removed oxidatively with DDQ in the presence of Bn ethers; the same orthogonality is seen with PSB ethers (FIG. 5). Alternatively, treating an equimolar mixture of 3c and 10 with basic peroxide affects only the PSB ether, leaving the PMB group intact.

Thus, the para-siletanylbenzyl PG has been shown to protect phenols and primary alcohols cleanly. It's easy removal under mild oxidative conditions as well as its orthogonality with the PMB group can be advantageous in multi-step synthesis.

2-Benzyloxy-1-methylpyridinium triflate as a Benzylating Protective Group

Synthesis and Isolation of Pyridinium Salt 1.

Figure 8:
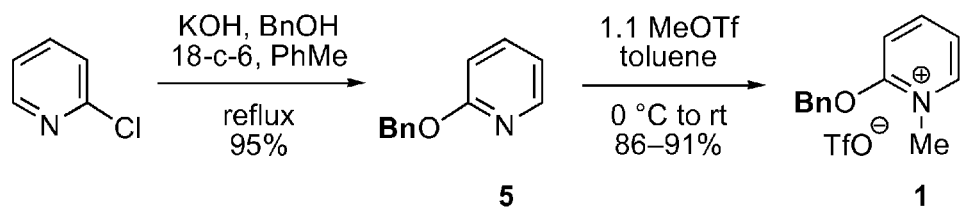
FIG. 8 shows the reaction for synthesis of compound 1,2-benzyloxy-1-methylpyridinium triflate.

The synthesis of 1 is illustrated in FIG. 8. Benzyl alcohol is coupled with 2-chloropyridine using a modification of a reported procedure to afford 2-benzyloxypyridine, compound 5, in high yield. A range of alkylating agents and solvents was investigated in search of preferred conditions for the irreversible covalent activation of 5. The preferred protocol is to add methyl triflate (bp 94-99° C.) to an ice-cold solution of compound 5 in toluene and allow the mixture to warm to ambient temperature. A white microcrystalline solid, compound 1, forms within minutes, as the solution warms. Analytically pure compound 1 (mp 82-86° C.) can be isolated by filtration or by evaporation of the supernatant under reduced pressure. Salt 1 is remarkably stable. It may be preferably stored under an argon atmosphere either in a refrigerator or on the laboratory bench-top at room temperature and the white crystals of compound 1 are routinely handled open to the air. No differences have been observed between freshly prepared crystals and those that were prepared three months prior.

Development and Analysis of a Benzylation Protocol.

At room temperature, the title reagent is freely soluble in chlorinated solvents such as dichloromethane, chloroform and dichloroethane; it is partially soluble in ethereal solvents such as THF and ether; and it is insoluble in aromatic hydrocarbons such as benzene and toluene. Solutions of compound 1 and 3-phenylpropanol, 2a as shown in Table 3, provided the desired benzyl ether upon heating. Because of its ability to solvate compound 1 and its convenient boiling point (83° C.), the initial investigation of reaction conditions was conducted in dichloroethane (DCE).

A first consideration was the presumed mild acidity of hydroxypyridinium triflate 4 (Table 3). Among the various acid scavengers investigated, heterogeneous inorganic salts appeared most compatible with the desired benzylation reaction (Table 3, entries 3-5). Soluble amines appeared to interfere with the coupling reaction (Table 3, entries 1 and 2) and it was unclear whether external amine bases would present any advantage in terms of moderating the potential acidity of pyridinium, compound 4. Based on these results and a cost analysis, magnesium oxide (MgO) emerged as a preferred choice. Thereafter, MgO was routinely included in all subsequent experiments.

Figure 9:
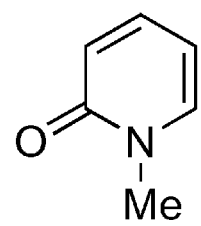
FIG. 9 shows byproduct compounds in the reaction shown in Table 3.
Figure 9:
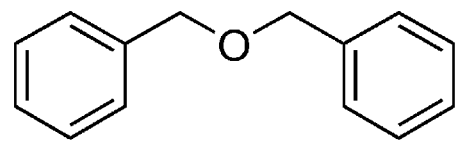

In addition to the desired benzyl ether, two byproducts were observed in the crude product mixture, as seen in FIG. 9: 1-methyl-2-pyridone (compound 6) and dibenzyl ether ($Bn_2O$, compound 7). Pyridone 6, the conjugate base of hydroxypyridinium 4, is the expected byproduct of benzylation reactions using compound 1. Pyridone 6 is freely water-soluble and easily removed by aqueous extraction. The source of $Bn_2O$ is not fully understood but it is thought that it may derive from reaction of compound 1 with MgO, although small amounts of 7 were also observed during control experiments that did not include MgO. It is theorized that adventitious moisture may be partly responsible for the formation of 7. Because dibenzyl ether is unlikely to interfere with most benzylation reactions, presence of a small amount of this byproduct is not considered to be a serious concern. Nonetheless, it was difficult to separate 7 from many of the alkyl benzyl ethers generated during the course of these investigations.

Figure 10:
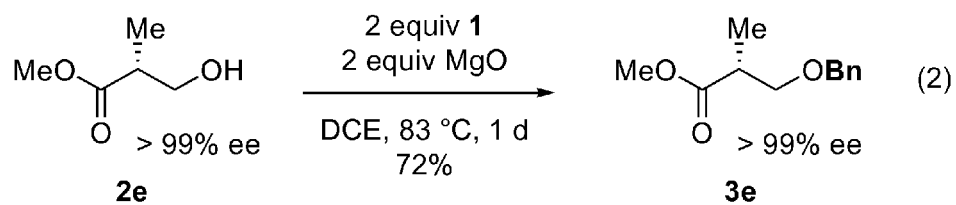
FIG. 10 shows a reaction for benzylation of chiral β-hydroxy ester 2e.

A test indicative of the efficacy of compound 1 in the invention was the benzylation of chiral β-hydroxy ester 2e (seen in the formula of FIG. 10). Benzyl ethers derived from such chiral alcohols are difficult to obtain under Williamson ether conditions because of the potential both for β-elimination and/or for epimerization of the labile stereogenic center α- to the ester. Benzylation using compound 1 proceeded efficiently (2e→3e) with no evidence of epimerization detectable by chiral HPLC analysis. Benzyl ether 3e was easily separated from $Bn_2O$ by chromatography on silica gel. A series of primary and secondary alcohols were benzylated under similar conditions and with similar efficiencies (70-76% yield). These results were reported by Poon, K. W. C.; House, S. E. and Dudley, G. B., in *Synlett* 2005, 3142-3144, which publication is incorporated herein by reference in its entirety.

Despite limited solubility, mixtures of compound 1 in many solvents became homogeneous upon warming, especially as the temperatures approached the melting point of compound 1 (82-86° C.). Toluene emerged as a promising preferred solvent in small-scale exploratory experiments. Therefore, various aromatic solvents, as shown in Table 4. Yields improved significantly in aromatic hydrocarbon solvents relative to dichloroethane (>90% vs. 67%).

Figure 12:
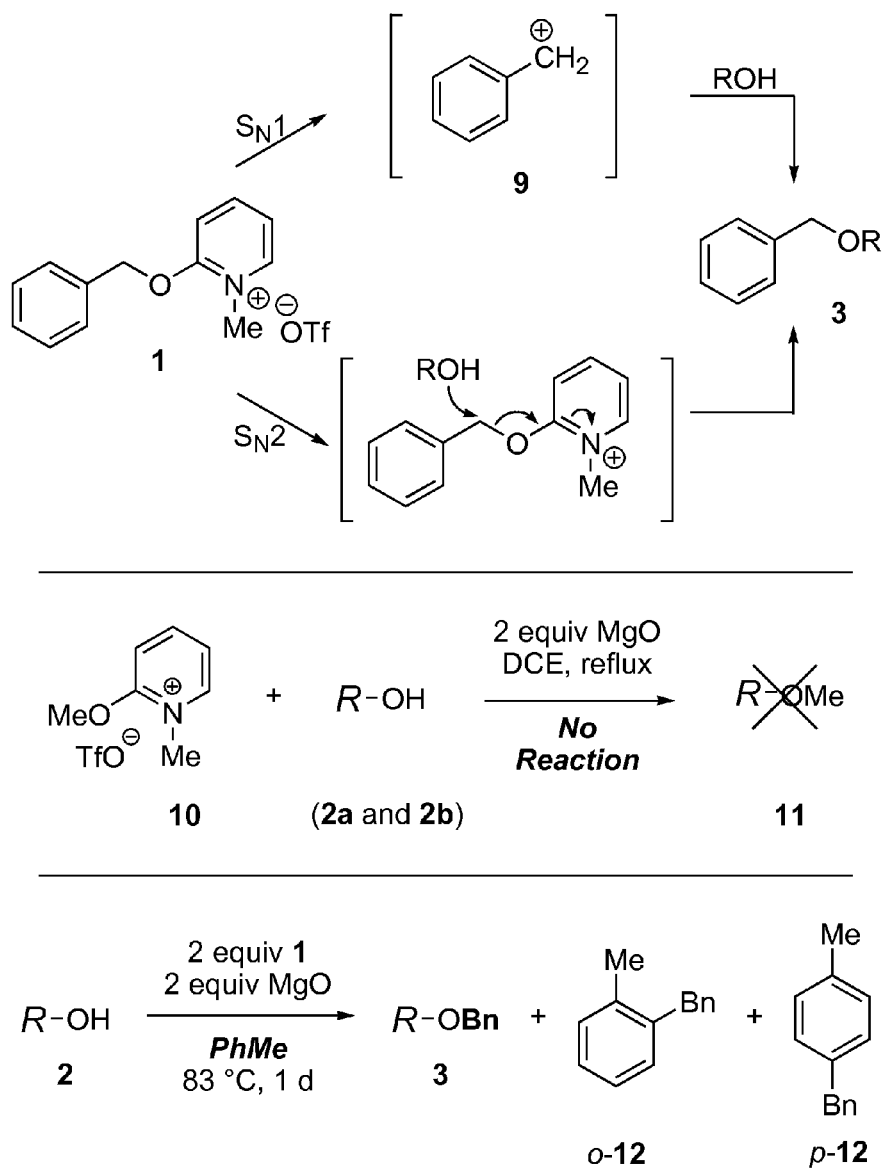
FIG. 12 shows proposed mechanisms for the benzylation according to an embodiment of the present invention.

Reactions conducted in toluene and, to a lesser extent, benzene and chlorobenzene, gave rise to trace amounts of benzylated solvent molecules (FIG. 12). No such products were observed from reactions conducted in benzotrifluoride (α,α,α-trifluorotoluene, $PhCF_3$).

In addition to being an excellent solvent for the present benzylation reactions, benzotrifluoride is low-cost, moderately volatile (bp 100-103° C.), and highly regarded as an environmentally friendly alternative to chlorinated solvents. Benzotrifluoride is the preferred choice as solvent for the benzylation reactions, although Table 4 indicates that other aromatic hydrocarbons are also suitable and these are intended to be included within the scope of the invention.

Figure 11:
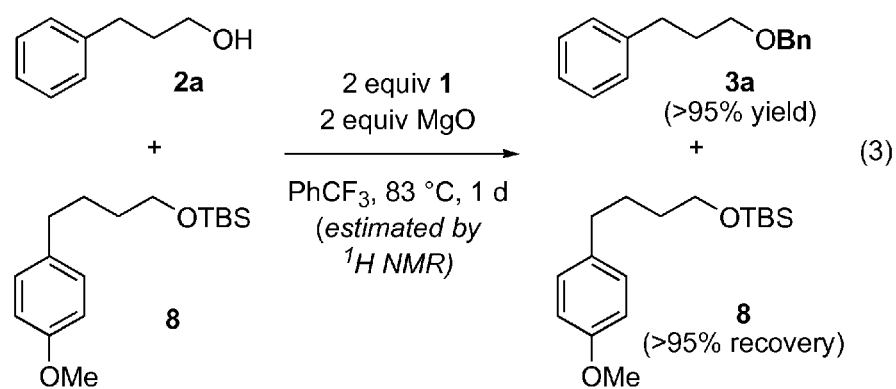
FIG. 11 depicts a benzylation reaction according to the present invention in the presence of a primary silyl ether.

Having identified a preferred solvent, acid scavenger, and time and temperature, the scope and limitations of what are considered to be mild and effectively neutral benzylation conditions was explored. The tolerance of this protocol for sensitive functionality was indicated by a test of the herein disclosed benzylation reaction in the presence of a primary silyl ether, as shown in FIG. 11. The desired benzyl ether, compound 3a, was obtained in excellent yield and silyl ether, compound 8, was recovered unchanged.

Mix and Heat Benzylation of Alcohols: Scope and Limitations.

Table 5 illustrates the benzylation reactions of representative alcohols under preferred conditions as disclosed herein. Primary (entries 1-6) and secondary (entries 7-9) alcohols all provided the desired benzyl ethers (3a-h) in good to excellent yield. Among these substrates are an allylic alcohol (entry 4), a homo-allylic alcohol (entry 9), and a β-hydroxy ester (entry 6). No difference was detected between freshly prepared reagent and a sample of 1 that had been aged for three months (cf. entries 1 and 2).

Tertiary alcohols and phenols provided variable results (entries 10-12). 1-Adamantanol (2i), which is not prone to elimination, afforded benzyl ether 3i in good yield. Tertiary benzylic alcohol 2j, which is highly prone to elimination, provided only a moderate yield of ether 3j. These two substrates may approximate the upper and lower limits of benzylation efficiency for tertiary alcohol substrates using 1. Phenols (e.g., 2k, entry 12) reacted sluggishly in these tests, possibly due to a decrease in nucleophilicity relative to aliphatic alcohols. Because benzylation of phenols can be accomplished using Mitsunobu conditions, 19 this class of substrates was not investigated further.

Insights into the Potential Reaction Mechanism.

Without wishing to be bound thereby, the mechanistic course of benzylation reactions using 1 probably falls along the continuum between SN1 and SN2 pathways, as shown in FIG. 12. Although no detailed kinetic studies have been conducted, two key observations are more consistent with an SN1-type mechanism. Benzylation reactions conducted in toluene afforded trace amounts of o-12 and p-12. It is assumed that these compounds derive from Friedel-Crafts alkylation of toluene, which suggests the presence of benzyl cation (compound 9 in FIG. 12) in the reaction mixture and argues in favor of an SN1-type pathway. Methoxypyridinium salt 10 was completely inert under similar conditions, which argues against an SN2-type pathway. It is, therefore, concluded, again not wishing to be bound thereto, that benzylation using compound 1 is more likely to occur via the SN1 mechanism. This conclusion is consistent with behavior observed in trichloroacetimidate reactions.

Experimental Details.

Synthesis of 2-Benzyloxypyridine, compound 5 as shown in FIG. 8.

The following is a modification of a previously reported procedure according to a publication by Serio Duggan, A. J.; Grabowski, E. J. J.; and Russ, W. K. *Synthesis* 1980, 573-575. Said publication being incorporated herein by reference in its entirety. A mixture of benzyl alcohol (2.00 g, 18.5 mmol), 2-chloropyridine (3.46 g, 30.5 mmol), KOH (3.42 g, 61.0 mmol, ground with a mortar and pestle), toluene (37 mL), and 18-crown-6 (24.4 mg, 0.925 mmol) was heated at reflux for 1 h with azeotropic removal of water (Dean-Stark trap). The reaction mixture was then cooled to room temperature and partitioned between ethyl acetate (20 mL) and water (10 mL). The organics were washed (brine), dried ($Na_2SO_4$), filtered, concentrated under vacuum, and purified on silica gel (elution with 100:1 hexane/EtOAc) to provide 3.28 g of compound 5 (96% yield) as a yellow liquid.

Synthesis of 2-Benzyloxy-1-methylpyridinium triflate, Compound 1 as Shown in FIG. 8 and FIG. 12.

To a cold (0° C.) solution of 2-benzyloxypyridine (compound 5) (100 mg, 0.54 mmol) in toluene (0.540 mL) was added methyl trifluoromethanesulfonate (64 L, 0.57 mmol). The mixture was allowed to warm to room temperature, which resulted in the formation of a white crystalline precipitate. After 40 min, the volatiles were removed in vacuo, providing 0.172 g (91% yield) of 1 as a white microcrystalline solid, mp: 82-86° C. A similar large-scale experiment afforded 6.52 g (86% yield) of 1 as a white solid, which was collected by filtration of the crude reaction mixture through a fritted glass funnel, followed by drying under vacuum. $^1$H NMR (300 MHz, $CDCl_3$) δ 8.49 (d, J=7.8 Hz, 1H), 8.34 (apparent t, J=8.3 Hz, 1H), 7.59 (d, J=9.0 Hz, 1H), 7.53-7.42 (m, 6H), 5.58 (s, 2H), 4.13 (s, 3H);

$^{13}$C NMR (75 MHz, $CDCl_3$) 159.6, 148.0, 143.8, 132.5, 129.6, 129.1, 128.5, 119.0, 112.1, 74.5, 42.0. HRMS (ESI$^+$) found 200.10704 (M-OTf)$^+$ (calcd for $C_{13}H_{14}NO^+$: 200.1075).

Another, perhaps more traditional formula depicting the compound of the invention (compound 1 shown in FIGS. 8 and 12) is as follows:

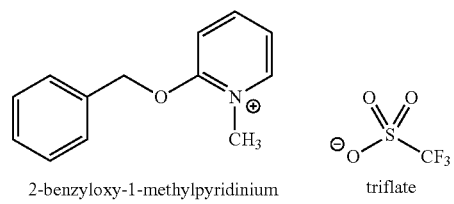

2-benzyloxy-1-methylpyridinium         triflate

Standard Procedure for Benzylation of Alcohols (2→3).

A mixture of pyridinium triflate 1 (100 mg, 0.29 mmol), benzotrifluoride ($PhCF_3$, 0.29 mL), MgO (11.5 mg, 0.29 mmol, vacuum-dried), and alcohol 2 (0.14 mmol) was heated at 83° C. for 1 day. The reaction mixture was cooled to room temperature and filtered through Celite®. The filtrate was concentrated under vacuum and purified on silica gel to yield benzyl ether 3 (see Table 5), admixed with varying amounts of $Bn_2O$.

Benzylation of Diethylene Glycol Monomethyl Ether (Monoglyme, Compound 2d)

A mixture of pyridinium triflate 1 (581 mg, 1.67 mmol), benzotrifluoride ($PhCF_3$, 1.7 mL), MgO (67 mg, 1.7 mmol), and compound 2d (100 mg, 0.83 mmol) was subjected to the standard procedure to afford 0.163 g (93%) of diethylene glycol benzyl methyl ether (compound 3d) as a pale yellow liquid, which exhibited spectroscopic properties consistent with the reported data.

Benzylation of 1-adamantanol (2i).

A mixture of pyridinium triflate 1 (100 mg, 0.29 mmol), benzotrifluoride ($PhCF_3$, 0.29 mL), MgO (11.5 mg, 0.29 mmol), and 28 (21.8 mg, 0.14 mmol) was subjected to the standard procedure to afford 0.0363 g of a yellow oil, which was determined by $^1$H NMR analysis to consist of 8.7 mg of $Bn_2O$ and 0.0276 g (80%) of 1-benzyloxyadamantane (3i). Spectroscopic analysis was consistent with the data reported previously for 3i.

Benzylation of Trimethylsilylethanol.

Figure 13:
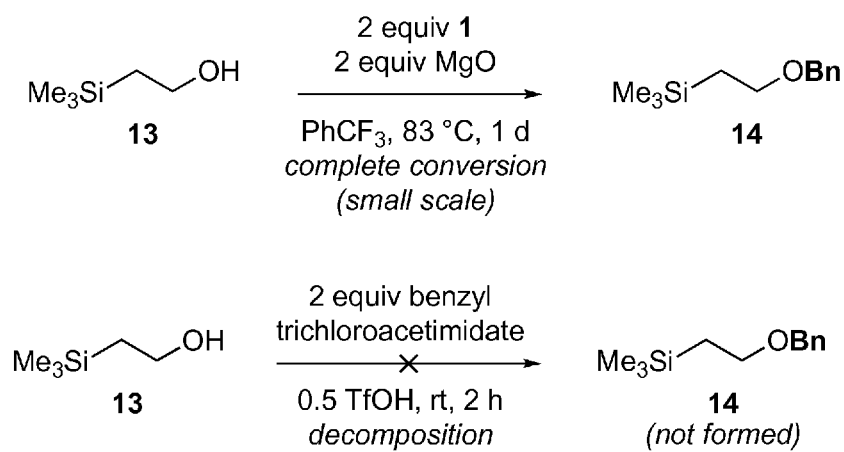
FIG. 13 in the top panel shows the reaction according to the present invention and in the lower panel shows a similar reaction but which fails to produce the desired end product.

In order to show the advantage of the present invention and, specifically of compound 1 herein, an experiment was con ducted using trimethylsilylethanol (compound 13) as a substrate for benzylation. Note that compound 13 is subjected to Peterson elimination under acidic (or basic) conditions; see Ager, D. J. in *Org. React.*, 1990, 38, 1. Benzylation of trimethylsilylethanol, that is, the conversion 13→14 as shown in FIG. 13, has not been previously reported. Reaction of 13 with 1 proceeded to complete conversion with no evidence of decomposition, whereas a similar experiment using benzyl trichloroacetimidate yielded no evidence of the desired product (compound 14). This is supported by the $^1$H NMR spectra obtained of the crude product mixtures after aqueous workup.

In summary, the present invention provides compounds and methods for arylmethylation (benzylation) as protection for alcohol groups during chemical synthesis. The protection is easily and economically effected and reactants are also equally easily deprotected once the synthetic process has been completed.

Accordingly, in the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

TABLE 1

Protection of phenols and alcohols as PSB ethers.

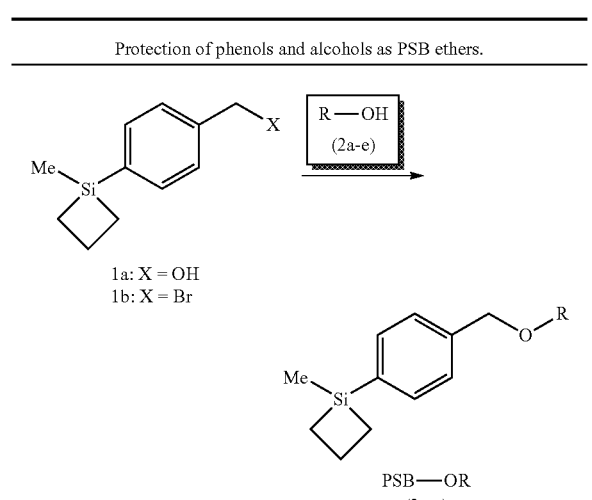

1a: X = OH
1b: X = Br

PSB—OR
(3a-e)

| entry | PSB-X | alcohol | conditions[a] | PSB ether (% yield) |
|---|---|---|---|---|
| 1 | 1a | 2a | A | 3a (74) |
| 2 | 1b | | B | — |
| 3 | | | C | 3a (70) |
| 4 | 1a | 2b | A | 3b (96) |
| 5 | 1b | 2c | C | 3c (80-83) |
| 6 | | | B | — |
| 7 | | 2d | C | 3d (50) |
| 8 | | 2e | C | 3e (38) |

[a]Conditions: A: PPh$_3$, DEAD, CH$_2$Cl$_2$; B: K$_2$CO$_3$/TBAI, Cs$_2$CO$_3$, or NaH, DMF; C: Ag$_2$O, CH$_2$Cl$_2$

TABLE 2

Cleavage of PSB ethers.

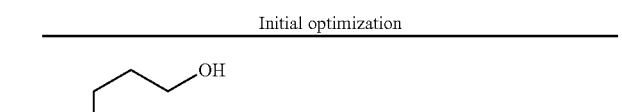

| entry | PSB ether | conditions[a] | PHB ether (% yield) | alcohol (% yield) |
|---|---|---|---|---|
| 1 | 3a | D | — | 2a (89) |
| 2 | 3b | | — | 2b (86) |
| 3 | 3c | i. D | 4c (87) | 2c (99) |
| 4 | 3d | ii. FeCl$_3$ | 4d (84) | 2d (97) |
| 5 | 3e | | 4e (85) | 2e (94) |
| 6 | 3c | i. E; ii. DDQ | 4c (99) | 2c (90) |
| 7 | 3d | i. E; ii FeCl$_3$ | 4d (99) | 2d (97) |
| 8 | 3e | F | — | 2c (88) |

[a]Conditions: D: K$_2$CO$_3$, KF•2H$_2$O, 30% aqueous H$_2$O$_2$, THF/MeOH, 50° C.;[16] E: TBAF, tBuOOH, DMF, 70° C.; F: H$_2$, 10% Pd/C.

TABLE 3

Initial optimization

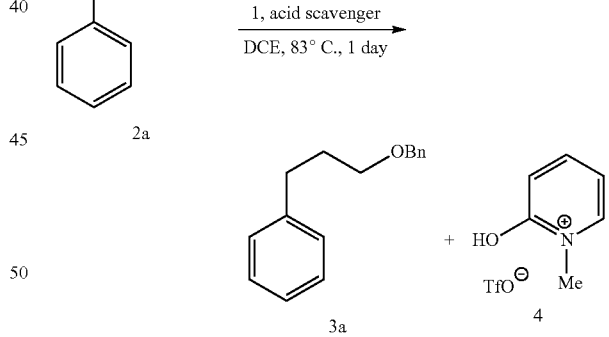

| entry | acid scavenger | equiv. 1 | yield[b,c] |
|---|---|---|---|
| 1 | 2,6-lutidine | 1.0 | 43% (57%) |
| 2 | Hünig's base | 1.0 | 29% (39%) |
| 3 | K$_2$CO$_3$ | 1.0 | 68% (93%) |
| 4 | MgO | 1.0 | 78% (93%) |
| 5 | — | 1.0 | 53% (87%) |
| 6 | MgO | 2.0 | 76% (85%) |
| 7 | MgO | 3.0 | 87% |

[a]See Supporting Information for details.
[b]Value in parenthesis refers to calculated yield based on recovered alcohol.
[c]Estimated by $^1$H NMR spectroscopy.

TABLE 4
Screening for optimal solvent
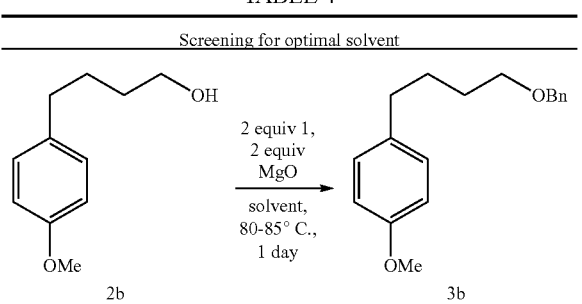
| entry | solvent | yield[a] |
|---|---|---|
| 1 | 1,2-dichloroethane (DCE) | 67% |
| 2 | nitromethane | (low) |
| 3 | acetonitrile | — |
| 4 | N-methyl-2-pyrrolidinone (NMP) | — |
| 5 | toluene | 91% |
| 6 | benzene | 93% |
| 7 | chlorobenzene | >95% |
| 8 | benzotrifluoride (PhCF$_3$) | >95% |
[a]Estimated by $^1$HNMR spectroscopy
TABLE 5
Scope and limitations
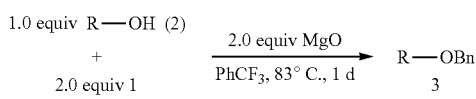
| entry | ROH (2) | ROBn (3) | yield[a] |
|---|---|---|---|
| 1 | 2a | 3a | >95% |
| 2[b] | 2a | 3a | >95% |
| 3 | 2b | 3b | >95% |
| 4 | 2c | 3c | n.d.[c] |
| 5 | 2d | 3d | 93%[d] |
| 6 | 2e | 3e | 85% |
| 7 | 2f | 3f | 83% |
| 8 | 2g | 3g | 88% |

TABLE 5-continued

Scope and limitations $$\text{1.0 equiv R—OH (2)} + \text{2.0 equiv 1} \xrightarrow[\text{PhCF}_3, 83°\text{C., 1 d}]{\text{2.0 equiv MgO}} \text{R—OBn} \quad 3$$

| entry | ROH (2) | ROBn (3) | yield[a] |
|---|---|---|---|
| 9 | 2h (cholesterol, HO-) | 3h (cholesterol, BnO-) | n.d.[c] |
| 10 | 2i (1-adamantanol) | 3i (1-adamantyl OBn) | 80% |
| 11 | 2j (PhC(Me)₂OH) | 3j (PhC(Me)₂OBn) | 44% |
| 12 | 2k (Ph-C₆H₄-OH) | 3k (Ph-C₆H₄-OBn) | 65%[e] |

[a]Yields are estimated by ¹H NMR spectroscopy, unless otherwise indicated.
[b]Reagent 1 stored for three months at room temperature before use.
[c]Not determined.
[d]Isolated yield of pure product.
[e]Unreacted 2k also observed in crude product mixture.

That which is claimed:

1. A method of protecting a reactant's alcohol group prior to an organic chemical synthesis, the method comprising warming the reactant in the presence of 2-benzyloxy-1-methylpyridinium triflate so as to benzylate the alcohol group with formation of a benzyl ether.

2. The method of claim 1, wherein a warming temperature is 80° C. to 85° C.

3. The method of claim 1, further comprising warming the reactant in the presence of an inorganic salt acid scavenger.

4. The method of claim 3, wherein the inorganic salt acid scavenger is MgO.

5. The method of claim 1, wherein warming the reactant is performed in an aromatic solvent.

6. The method of claim 1, wherein warming the reactant is performed in a chlorinated solvent.

* * * * *